United States Patent [19]

Lucas et al.

[11] Patent Number: 5,328,695

[45] Date of Patent: Jul. 12, 1994

[54] MUSCLE MORPHOGENIC PROTEIN AND USE THEREOF

[75] Inventors: Paul A. Lucas; Henry E. Young, both of Macon, Ga.; Cato T. Laurenchin, Somerville, Mass.

[73] Assignee: Massachusetts Institute of Technology, Cambridge, Mass.

[21] Appl. No.: 835,727

[22] Filed: Feb. 11, 1992

Related U.S. Application Data

[63] Continuation-in-part of Ser. No. 742,264, Aug. 7, 1991, abandoned, and a continuation-in-part of Ser. No. 810,324, Dec. 19, 1991, abandoned, and a continuation-in-part of Ser. No. 61,294, Jun. 19, 1987, Pat. No. 4,888,176, which is a continuation-in-part of Ser. No. 892,809, Aug. 1, 1986, Pat. No. 4,757,128, which is a continuation-in-part of Ser. No. 613,001, May 21, 1984, Pat. No. 4,906,474, said Ser. No. 742,264, is a continuation of Ser. No. 313,953, Feb. 22, 1989, abandoned, said Ser. No. 810,324, is a continuation of Ser. No. 690,042, Apr. 23, 1991, abandoned, which is a continuation of Ser. No. 361,222, Jun. 5, 1989, abandoned, which is a continuation-in-part of Ser. No. 613,001, Jun. 5, 1989, which is a continuation of Ser. No. 477,710, Mar. 22, 1983, abandoned.

[51] Int. Cl.⁵ .................. A61K 37/02; A61K 37/12; A61F 2/08; C07K 15/28
[52] U.S. Cl. .................. 424/426; 424/423; 514/2; 514/21; 530/300; 530/353; 530/840; 623/14
[58] Field of Search .................. 424/423, 426; 514/2, 514/21; 530/300, 353, 840; 623/14

[56] References Cited

U.S. PATENT DOCUMENTS

| | | | |
|---|---|---|---|
| 4,434,094 | 2/1984 | Seyedin et al. | 530/840 |
| 4,757,128 | 7/1988 | Domb et al. | 528/271 |
| 4,774,322 | 9/1988 | Seyedin et al. | 530/840 |
| 4,789,732 | 12/1988 | Urist | 530/840 |
| 4,888,176 | 12/1989 | Langer et al. | 424/426 |
| 4,906,474 | 3/1990 | Langer et al. | 424/428 |
| 5,011,691 | 4/1991 | Opperman et al. | 530/840 |
| 5,106,626 | 4/1992 | Parsons et al. | 530/840 |

FOREIGN PATENT DOCUMENTS

WO90/09783 7/1990 PCT Int'l Appl. .
WO90/15586 12/1990 PCT Int'l Appl. .

OTHER PUBLICATIONS

Carlson, B. M. and J. A. Faulkner, "The regeneration of skeletal muscle fibers following injury: a review," 15(3) *Med. Sci. Sports & Exercise* 187–198 (1983).

Buckley, A., et al., "Sustained release of epidermal growth factor accelerates wound repair," 82 Proc. Natl. Acad. Sci. USA 7340–7344 (Nov. 1985).

Davidson, J., et al. "Mechanisms of accelerated wound repair using epidermal growth factor and basic fibroblast growth factor," Proc. Second Intern'l Symp. on Tissue Repair, in *Growth factors and other aspects of wound healing: Biological and clinical implications*, A. Barbul et al., eds., Alan R. Liss, New York, pp. 63–75 (1988).

(List continued on next page.)

Primary Examiner—Thurman K. Page
Assistant Examiner—Carlos Azpuru
Attorney, Agent, or Firm—Kilpatrick & Cody

[57] ABSTRACT

A myogenic protein isolate from mammalian bone is provided that stimulates lineage commitment and differentiation of stem cells in vitro and in vivo. The protein isolate is characterized by its ability to cause muscle stem cell differentiation without excessive proliferation of connective tissue proximal to the delivery site. Treated muscle stem cells differentiate into myotubes and multinucleated structures with minimal formation of scar tissue, resulting in functional muscle tissue restoration in vivo, and therefore useful in the treatment of a number of disorders and injuries. The protein isolate is preferably administered by implanting a bioerodible polymer matrix, preferably a surface erodible polymer such as a polyanhydride or a polyorthoester, interspersed with the protein isolate near the site of muscle injury or degeneration, but can be administered directly to cells cultured in vitro.

10 Claims, No Drawings

OTHER PUBLICATIONS

Donovan, C. M., and J. A. Faulkner, "Plasticity of skeletal muscle: regenerating fibers adapt more rapidly then surviving fibers," 62(4–6) *J. App. Phys.* 1345–2543 (1987).

Ewton, D. Z., and J. R. Florini, "Effects of insulin-like growth factors and transforming growth factor-beta on the growth and differentiation of muscle cells in culture," 194(2) *Proc. Soc. Exp. Biol. Med.* 76–80 (Jun. 1990).

Ewton, D. Z., and J. R. Florini, "Effects of the somatomedins and insulin on myoblast differentiation in vitro", 86 *Dey. Biol.* 31–39 (1981).

Faulkner, J. A. and B. M. Carlson, "Skeletal muscle regeneration: a historical perspective," 45(5) *Fed. Proc.* 1454–1455 (Apr. 1986).

Florini, J. R., et al., "Transforming growth factor-β: A very potent inhibitor of myoblast differentiation, identical to the differentiation inhibitor secreted by buffalo rat liver cells," 261 *J. Biol. Chem.* 16509–16513 (Dec. 15, 1986).

Florini, J. R., et al., "Biphasic concentraton dependency of stimulation of myoblast differentiation by somatomedins," 250(15) *Amer. J. Physiol.* C771–C778 (May 1986).

Franklin, T. J., et al., "Acceleration of wound healing by recombinant human urogastrone (epidermal growth factor)," 108(2) *J. Lab. Clin. Med.* 103–108 (Aug. 1986).

Grotendorst, G. R., et al., "Stimulation of granulation tissue formation by platelet-derived growth factor in normal and diabetic rats", 76 *J. Clin. Invest.* 2323–2329 (Dec. 1985).

Lim, R. W., and S. D. Hauschka, "A rapid decrease in epidermal growth factor-binding capacity accompanies the terminal differentiation of mouse myoblasts in vitro," 98 *J. Cell Biol.* 739–747 (1984).

Linkhart, T. A., et al., "Control of mouse myoblast commitment to terminal differentiation by mitogens," in *Muscle Development: Molecular and Cellular Control*, M. L. Pearson and H. F. Epstein, eds., Cold Spring Harbor Laboratory, New York, pp. 377–382 (1982).

Linkhart, T. A., et al., "Myogenic differentiation in permanent clonal mouse myoblast cell lines: Regulation by macromolecular growth factors in the culture medium," 86 *Dev. Biol.* 19–30 (1981).

Mustoe, T. A., et al., "Accelerated healing of incisional wounds in rats induced by transforming growth factor-beta," 237 *Science* 1333–1336 (Sep. 11, 1987).

Olwin, B. B., and S. D. Hauschkla, "Identification of the fibroblast growth factor receptor os Swiss 3T3 cells and mouse skeletal muscle myoblasts," 25(12) *Biochemistry* 3487–3492 (Jun. 17, 1986).

Reddi, A. H., and C. Huggins, "Biochemical sequences in the transformation of normal fibroblsts in adolescent rats," 69 *Proc. Nat. Acad. Sci. USA* 1601–1605 (Jun. 1972).

Roberts, A. B., et al., "Transforming growth factor type β: Rapid induction of fibrosis and angiogenesis in vivo and stimulation of collagen formation in vitro," 83(11) *Proc. Natl. Acad. Sci. USA* 4167–4171 (Jun. 1986).

Sejersen, T., et al., "Rat skeletal myoblasts and arterial smooth muscle cells express the gene for the A chain but not the gene for the B chain (c-sis) of platelet-derived factor (PDGF) and produce a PDGF-like protein," 83 *Proc. Natl. Acad. Sci. USA* 6844–6848 (Sep. 1986).

Sprugel, K. H., et al., "Effects of growth factors in vivo, I. Cell ingrowth into porous subcutaneous chambers," 129(3) *Amer. J. Pathol.* 601–613 (Dec. 1987).

Urist, M. R., et al., "Osteogenetic competence," 64 *Clin Orthopaed. Rel. Res.* 194–220 (May–Jun. 1969).

Urist, M. R., "Bone: Formation by autoinduction," 150 *Science* 893–899 (Nov. 12, 1965).

Young, H. E., et al., "Glycoconjugates in normal wound tissue matrices during the initiation phase of limb regeneration in adult Ambystoma," 223 *Anat. Rec.* 231–241 (1989).

Bader, D., et al., "Immunochemical analysis of myosin heavy chain during avian myogenesis in vivo and in vitro," 95 *J. Cell Biol.* 763–770 (Dec. 1982).

Bischoff, R., "Proliferation of muscle satellite cells on intact myofibers in culture," 115 *Dev. Biol.* 129–139 (1986).

Bischoff, R., "A satellite cell mitogen from crushed adult muscle," 115 *Dev. Biol.* 140–147 (1986).

Bischoff, R., "Tissue culture studies on the origin of myogenic cells during muscle regeneration in the rat," pp. 13–29, in *Muscle Regeneration*, A. Mauro et al., ed., Raven Press, New York (1979).

Carlson, B. M., "The regeneration of skeletal muscle–A review," 137 *Am. J. Anat.* 119–150 (May–Jul. 1979).

(List continued on next page.)

OTHER PUBLICATIONS

Schultz, E., et al., "Response of satellite cells to focal skeletal muscle injury," 8 *Mucscle and Nerve* 217–222 (Mar.–Apr. 1985).

Schultz, E., "A quantitative study of satellite cells in regenerated soleus and extensor digitorum longus muscles," 208 *Anat. Rec.* 501–506 (Jan.–Apr. 1984).

Snow, M. H., "Myogenic cell formation in regenerating rat skeletal muscle injured by mincing: A fine structural study," 188(2) *Anat. Rec.* 181–199 (Jun. 1977).

Snow, M. H., "Myogenic cell formation in regeneration rat skeletal muscle injured by mincing: An autoradiographic study," 188 *Anat. Rec.* 210–217 (May–Aug. 1977).

Young, H. E., et al., "Cryopreservation of embryonic chick myogenic lineage-committed stem cells," 13 *J. Tiss. Cult. Meth.* 275–288 (1991).

Young, H. E., et al., "Comparison of fixatives for maximal retention of radiolabeled glycoconjugates for autoradiography, including use of sodium sulfate to release unicorporated [$^{36}$]-sulfate," 37(2) *J. Histochem. Cytochem.* 223–228 (1989).

Young, H. E., et al., "Initial characterization of small proteoglycans synthesized by embryonic chick leg muscle-associated connective tissues," 17 *Connec. Tiss. Res.* 99–118 (1989).

Young, H. E., et al., "Histochemical analyusis of newly synthesized and accumulated sulfated glycosaminoglycans during musculogenesis in the embryonic chick leg," 201 *J. Morph.* 85–103 (1989).

Young, H. E., et al., "Histological analysis of limb regeneration in postmetamorphic adult Ambystoma," 212 *Anat. Rec.* 183–194 (1985).

Florini, J. R., et al., "Hormones, growth factors, and myogenic differentiation," 53 *Ann. Rev. Physiol.* 201–216 (1991).

MUSCLE MORPHOGENIC PROTEIN AND USE THEREOF

This is a continuation in part of U.S. Ser. No. 742,264 entitled "Delivery System for Controlled Release of Bioactive Factors" filed Aug. 7, 1991 by Cato T. Laurencin, Paul A. Lucas, Glenn T. Syftestad, Abraham J. Domb, Julie Glowacki and Robert S. Langer, now abandoned which is a continuation of U.S. Ser. No. 07/313,953 filed Feb. 22, 1989 now abandoned; a continuation in part of U.S. Ser. No. 07/810,324 entitled "Bioerodible Polymers for Drug Delivery in Bone" filed Dec. 19, 1991 by Tobin N. Gerhart, Cato T. Laurencin, Abraham J. Domb, Robert S. Langer, and Wilson C. Hayes, now abandoned, which is a continuation of U.S.S.N. 07/690,042 filed Apr. 23, 1991, now abandoned, which is a continuation of U.S.S.N. 07/361,222 filed Jun. 5, 1989, which is a continuation-in-part of U.S. Ser. No. 613,001 entitled "Bioerodible Polyanhydrides for Controlled Drug Delivery" filed May 21, 1984 by Robert S. Langer, Howard Rosen, Robert J. Linhardt, and Kam Leong, now U.S. Pat. No. 4,906,474, which is a continuation of U.S. Ser. No. 06/477,710 filed Mar. 22, 1983, now abandoned; and a continuation-in-part of U.S. Ser. No. 07/061,294 entitled "Controlled Drug Delivery High Molecular Weight Polyanhydrides" filed Jun. 12, 1987, by Robert S. Langer, Edith Mathiowitz, Abraham J. Domb, and Cato T. Laurencin, now U.S. Pat. No. 4,888,176, which is a continuation-in-part of U.S. Ser. No. 06/892,809 filed Aug. 1, 1986, issued as U.S. Pat. No. 4,757,128 Jul. 12, 1988, which is a continuation-in-part of U.S. Ser. No. 06/613,001.

The present invention relates to the field of biochemistry and more particularly to a myogenic protein isolate and delivery thereof.

BACKGROUND OF THE INVENTION

Mammalian skeletal muscle normally undergoes a reparative process after traumatic injury. The process of skeletal muscle repair is actually a series of discrete overlapping events, which can be segregated into trauma, tissue degeneration, inflammation, phagocytosis, angiogenesis, stem cell activation, migration of the stem cells to the site of injury, proliferation of undifferentiated stem cells, reinnervation, differentiation of the stem cells, and remodelling of the tissue.

The early restored muscle tissues approximate embryonic-like myotubes containing centrally-located nuclei and lie adjacent to mature myofibers containing peripherally-located nuclei. Unfortunately, restoration of physiological function is compromised due to the increased proliferative nature of the surrounding connective tissues, eventually forming non-functional scar tissue.

To circumvent the decreased function due to scar tissue formation, Carlson and Faulkner, Med. Sci. Sports Exerc. 15:187-198 (1983); Faulkner and Carlson, Fed. Proc. 45:1454 (1986); and Donovan and Faulkner, J. Appl. Physiol. 62:2507-2511 (1987) severed existing vascular and nervous tissue connections prior to grafting homologous and autologous muscles. This procedure apparently inhibited myogenic differentiation of cultured cells and Faulkner and colleagues reported some restoration of function using it.

Research in other areas has indicated that various factors such as platelet derived growth factor (PDGF), chicken muscle growth factor (CMGF), epidermal growth factor (EGF), sciatic nerve extract, insulin, and somatomedins stimulate a mitogenic or proliferative response in cultured muscle cells. This response should be contrasted with a myogenic response which does not induce myogenic lineage commitment of uncommitted stem cells, but instead induces the lineage commitment of the stem cells.

Three growth factors, insulin and insulin-like growth factors, namely insulin-like growth factor-I (IGF-I), also called somatomedin-C, insulin-like growth factor-II (IGF-II), also called myogenic stimulating activity, have been shown to be potent stimulators of skeletal muscle cell growth and differentiation in cultured myosatellite cells and myogenic lineage-committed stem cells by Ewton and Florini, Dev. Biol. 83:31-39 (1981); Florini et al., J. Biol. Chem. 261:16509-16515 (1986); Florini et al., Am. J. Physiol. 250:C771-778 (1986); Sejersen et al., Proc. Natl. Acad. Sci. 83:6844-6848 (1986); Ewton et al., Fed. Proc. 45:1454-1455 (1987).

Several in vivo studies have employed basic-fibroblast growth factor (b-FGF), transforming growth factor beta (TGF-$\beta$), and epidermal growth factor (EGF) to stimulate internal wound healing. Buckley et al., Proc. Natl. Acad. Sci. 82:7340-7344 (1985); Grotendorst et al., J. Clin. Invest. 76:2323-2329 (1985); Franklin et al., J. Lab Clin. Med. 108:103-108 (1986); Roberts et al., Proc. Natl. Acad. Sci. 83:4167-4171 (1986); Mustoe et al., Science 1987; Sprugel et al., Am. J. Path. 129:601-613 (1987); and Davidson et al., Prog. Clin. Biol. Res. (1988) noted that administration of b-FGF, TGF-$\beta$B, and EGF appeared to promote proliferation of connective tissue elements to form scar tissue and thus aid in wound healing of mammalian skeletal muscle.

In vitro studies have demonstrated the influence of other growth factors on the resultant phenotypic expression in myogenic cultures. For example, Hauschka and co-workers have reported that acidic-fibroblast growth factor (a-FGF) and basic-fibroblast growth factor (b-FGF) play a dual role in stimulating myoblast proliferation while directly repressing terminal differentiation, as described by Linkhart et al., Dev. Biol. 86:19-30 (1981), the chapter of Linkhart et al. entitled "Control of mouse myoblast commitment to differentiation by mitogens." In: Molecular and Cellular Control of Muscle Development. M. L. Pearson and H. F. Epstein, eds., Cold Spring Harbor Laboratory, New York, p. 377-382 (1982); Lim and Hauschka, J. Cell Biol. 98:739-747 (1984); and Olwin and Hauschka, Biochemistry 25:3487-3492 (1986).

Unfortunately, the administration of growth factors that inhibit terminal myogenic differentiation, promote myoblast proliferation, and promote fibroblast proliferation and differentiation as a method to promote muscle repair appears to cause an increase in connective tissue scar formation. In muscle, increased scar formation creates decreased physiological function. A decrease in connective tissue scar formation with a compensatory increase in skeletal muscle mass plus revascularization and reinnervation of the tissues is necessary for the restoration of physiological function.

Implantation of demineralized bone into ectopic sites (i.e., intramuscular pouch, subcutaneous pouch) result in the induction of cartilage and bone within these tissues, as reported by Urist, Science 150:194-199 (1965); Urist et al., Clin. Orthopaed 64:194-220 (1969); and Reddi and Huggins, Proc. Nat. Acad. Sci. USA 69:1601-1605 (1972). Young et al, Anat. Rec.

223:231-241 (1989), demonstrated the existence of stem cells, arising from the connective tissues associated with muscle, cartilage, and bone, that contributed to the blastemal population during epimorphic limb regeneration in the adult terrestrial salamander. Combined, this work suggest the potential for the presence of quiescent uncommitted stem cells or quiescent lineage-committed stem cells located within or nearby these tissue matrices that upon the appropriate stimulus would form differentiated tissues. The stimulus or stimuli required for differentiation is not known.

A number of delivery systems have been proposed for administration of various drugs and other biologically active compounds. The most promising for practical reasons are the polymer based systems, as described, for example, for general drug delivery using the bioerodible polyanhydrides, in U.S. Pat. No. 4,906,474 to Langer, et al., U.S. Pat. No. 4,888,176 to Langer, et al., and U.S. Pat. No. 4,757,128 to Langer, et al. The more specific use of polymeric delivery systems for administration of antibiotics to bone is described in U.S. Ser. No. 07/810,324 entitled "Bioerodible Polymers for Drug Delivery in Bone" filed Dec. 19, 1991 by Gerhart, et al., the more specific delivery of osteogenic factors is described in U.S. Ser. No. 07/313,953 entitled "Delivery System for Controlled Release of Bioactive Factors" filed February 1989 by Laurencin, et al.

It would be advantageous if muscle morphogenic factors could be identified and delivered to the area around bone or in injured areas, especially if the factors are water soluble and likely to disperse rapidly in vivo, which would be useful in enhancing healing of muscle injuries without a concomitant increase in scarring.

It is therefore an object of the present invention to provide a myogenic differentiating composition.

It is a further object of the present invention to provide a method of restoring functional mammalian muscle with minimal scar formation.

It is another object of the present invention to provide a delivery system for a myogenic differentiating composition.

SUMMARY OF THE INVENTION

A myogenic protein isolate from mammalian bone is provided that stimulates lineage commitment and differentiation of stem cells in vitro and in vivo. The protein isolate is characterized by its ability to cause muscle stem cell differentiation without excessive proliferation of connective tissue proximal to the delivery site.

Treated muscle stem cells differentiate into myotubes and multinucleated structures with minimal formation of scar tissue, resulting in functional muscle tissue restoration in vivo, and therefore useful in the treatment of a number of disorders and injuries. The protein isolate is preferably administered by implanting a bioerodible polymer matrix, preferably a surface erodible polymer such as a polyanhydride or a polyorthoester, interspersed with the protein isolate near the site of muscle injury or degeneration, but can be administered directly to cells cultured in vitro.

DETAILED DESCRIPTION OF THE INVENTION

A myogenic protein isolate has been extracted from mammalian bone. The protein or proteins in the isolate are water soluble and have a molecular weight between 50,000 and 200,000 daltons as determined by SDS gel electrophoresis. The myogenic isolate causes lineage commitment and differentiation of stem cells in vivo and in vitro. Stem cells exposed to the myogenic isolate commit to the myogenic lineage, differentiate to form myoblasts, the myoblasts fuse to form myotubes, stellate-shaped cells, the myotubes increase in size, in vitro becoming branched or linear multinucleated myofibers, demonstrating synthesis of myosin that spontaneously contracts. When administered to a site of muscle injury or degeneration, the myogenic protein isolate stimulates the differentiation of both uncommitted and myosatellite stem cells into functional muscle tissue with minimal formation of scar tissue proximal to the site of muscle restoration.

EXTRACTION OF MYOGENIC PROTEIN ISOLATE

The myogenic protein isolate is generally extracted from mammalian bone with a solution such as guanidine hydrochloride, urea, 0.5 M EDTA, or sodium chloride in a concentration of at least 0.15 M as follows to remove materials such as albumin and $\alpha$2-macroglobulin, followed by demineralization with HCl or 0.5 NaCl, followed by extraction again with guanidine hydrochloride. The first extraction is not essential.

The protein can be isolated from bone of the same or different origin as the stem cells to be committed and differentiated, although in the preferred embodiment, protein of the same species of origin would be used.

The extract can be further purified by ultrafiltration with a YM10 membrane, passage over a DEAE-Sepharose TM column in urea where it is found in the unbound fraction, chromatography over a Sepharose TM CL6B column where it is found in those fractions with proteins of molecular weight greater than 50,000, salt gradient chromatography over a cation exchange column SP-Sephadex TM at pH 6.0, and heparin Sepharose chromatography, followed by reverse phase HPLC or electroelution from an SDS-PAGE or PAGE.

TREATMENT OF DISORDERS OR INJURIES WITH THE MYOGENIC PROTEIN ISOLATE

A wide variety of disorders or injuries can be treated with the myogenic protein isolate, alone or in combination with inducers of proliferation, such as one of the insulin growth factors, or other compounds, such as antibiotics or antiinflammatories. A preferred treatment is the treatment of wounds where the object is to enhance healing while minimizing scarring. Other diseases include muscular dystrophy, myasthenia gravis, multiple sclerosis, nerve block injuries, muscle atrophy, embryonic failure of myotomes to migrate, and rhabdomyosarcoma.

Examples of injuries or muscle weaknesses that can be treated include repair of aneurysms by increasing muscle bulk in the blood vessels, repair of hemorrhages by increasing muscle bulk around blood vessels, relief of ptosis (eye lid drep) by regeneration of non-damaged muscle in the eyelid, as well as tears in muscles and repair of muscle damaged by infarction, up to the point of growing new hearts or portions of heart muscle.

The myogenic protein can also be used to form new tissues for transplantation, where a limited amount from the donor is available, particularly in the case of autologous transplants.

The myogenic protein can be administered directly to the stem cells to induce commitment prior to injection back into the patient, or implanted in a controlled release device at a selected site containing stem cells to induce commitment and differentiation. Once the gene is isolated for the myogenic protein, this can also be inserted directly into cells to induce commitment and differentiation.

For treatment of most disorders where defective muscle cells are present, stem cells are obtained from normal donors, induced to proliferate to increase the population size, myogenesis induced, then they are injected into the diseased individual. In the case of wound treatment, the stem cells would preferably be obtained from the patient. Alternatively, the stem cells could be injected into the patient, then induced to differentiate.

ADMINISTRATION OF MYOGENIC PROTEIN ISOLATE

The muscle myogenic protein is administered to patients or cells in culture in combination with an acceptable pharmaceutical carrier. An effective dose in vivo will be generally in the range of between approximately 1 ng and 10 mg/kg, based on comparative studies with other known compounds.

Studies demonstrate that it is difficult to obtain a measurable effect in vivo using the isolate administered in solution. Preferably, the myogenic protein isolate is administered in a delivery vehicle that provides sustained or controlled release of the isolate. Most preferably, the protein isolate is interspersed throughout a bioerodible, surface-eroding polymer matrix which degrades in the biological environment, releasing the protein isolate to a site of requiring muscle restoration. The delivery vehicle can be directly added to an in vitro preparation or implanted in an animal for in vivo administration.

Surface-eroding polymers in general are polymers having hydrophobic backbones and hydrolytic linkages, which bioerode from the surface at a constant rate in a biological environment. Surface eroding polymers include polyanhydrides and polyorthoesters. Examples of polyanhydrides that can be used to deliver the myogenic protein isolate include poly[bis(p-carboxyphenoxy) propane anhydride] and poly[bis(p-carboxy) methane anhydride. Co-polymers of poly[bis(p-carboxyphenoxy) propane anhydride] and sebacic acid are useful examples.

Bulk erodible polymers are also useful. Examples include polylactic acid, polyglycolic acid, and copolymers thereof. Non-bioerodible polymers can also be used, for example, ethylene vinyl acetate (EVA), polyvinyl alcohol, polymethacrylate (PMA), nylon, teflon, and others that are approved for use in the body.

The protein isolate can be lyophilized and then dispersed with the polymer using mechanical mixing, during solvent evaporation, or using phase separation, techniques all known to those skilled in the art and described more specifically in the priority applications, the teachings of which are incorporated herein. Alternatively, the protein isolate can be mixed with the monomers and polymerized within the polymer prior to or at the time of implantation.

In another embodiment, the protein isolate is provided in a gel such as a Pluronic TM that is liquid at room temperature and soluble at body temperature and painted onto the muscle or injury where differentiation is desired. Pluronic TM gels are sold by BASF (New Jersey) that are liquid at 4° C. but solid at room temperature. Pluronic TM surfactants are polymers of ethylene oxide-propylene glycol-ethylene oxide repeating units. The properties of the polymer are dependent on the molecular weight of the polymer and relative percentage of polyoxyethylene to polyoxypropylene.

In still another embodiment, the protein isolate is provided in a transdermal patch, such as a modified bandage, so that wound healing occurs with decreased scarring.

The muscle morphogenetic protein isolate and method of delivery described generally above will be further understood with reference to the following non-limiting examples.

EXAMPLE 1: ISOLATIN OF MUSCLE MYOGENIC PROTEIN.

Mid-shaft femoral cortices of one year old steers (Shapiro Packing Co., Augusta, GA) were cleaned, ground into pieces less than 1 cm$^3$ in a hammer mill, defatted in chloroform:methanol (1:1) for 48 hours, rinsed with methanol, and air dried overnight to a constant weight. The bone chips were then extracted with a 4 M guanidine hydrochloride (GuHCl) solution, pH 7.0, containing protease inhibitors (382 g GuHCl, 6.05 g Tris TM Base, 0.625 g N-ethylmaleimide, 1 ml of 0.1 mM phenylmethylsulfonyl fluoride in 100% ethanol, and 0.33 g sodium azide with double distilled H$_2$O to 1 liter). Four ml of solution was added to each gram of bone and stirred for 96 hours followed by three extensive washes with double distilled H$_2$O.

The bone chips were decalcified at 4° C. by either a 0.6 N HCl solution or a 0.5 M ethylenediaminetetraacetate (EDTA) solution. The decalcifying solution contains the protease inhibitors in the guanidine solution, pH 7.0. The bone chips were re-extracted for five days at 4° C. in a solution of 4 M GuHCl buffered with 50 mM Tris TM, pH 6.8, containing the protease inhibitors described above. The resulting 4 M GuHCl extract was dialyzed at 4° C. sequentially against solutions of decreasing ionic strength: 0.5 M GuHCl, 50 mM Tris TM, and distilled water.

The EDTA extracts were pooled and concentrated into three aliquots of 300 ml each by Amicon TM ultrafiltration with a YM10 membrane. Each 300 ml EDTA aliquot was washed with five liters of double distilled H$_2$O. Precipitates formed at each step were removed by centrifugation until only those proteins soluble in cold distilled water remain. This portion of the extract was lyophilized and constitutes a water soluble myogenic protein isolate.

The lyophilized protein isolate was dissolved in 6 M urea, 50 mM Tris TM, 0.01% Triton TM X-100, pH 6.0, and the protease inhibitors described above. It was then passed over a DEAE-Sepharose TM column where it is found in the unbound fraction. The unbound fraction was then chromatographed over a Sepharose TM CL6B column and was found in those fractions with proteins of molecular weight greater than 50,000. Those fractions were then pooled and chromatographed over a cation exchange column SP-Sephadex TM at pH 6.0 and were found in the 0–0.2 M NaCl wash.

EXAMPLE 2: CHARACTERISTICS OF MYOGENIC PROTEIN ISOLATE

The myogenic protein isolate was analyzed by sodium dodecyl sulfate polyacrylamide electrophoresis (SDS-PAGE) g according to the method of Laemmli, *Nature* 277:680–685 (1970) using 10% acrylamide slab gels. Carbonic anhydrase (29,000), ovalbumin (45,000), and bovine serum albumin (68,000), were used as standards. After electrophoresis, slabs were fixed and stained for total protein using the silver stain procedure of Roberts et al., Analysis of membrane polypeptides by two-dimensional polyacrylamide gel electrophoresis. In: Molecular and Chemical Characterization of Membrane Receptors. J. Venter, Ed., Alan R. Liss, New York, Vol. 2, pp. 61–113 (1984).

The electrophoretic results indicated a major doublet at approximately 20,000 daltons, seven minor bands between 20,000 and 200,000 daltons, and numerous trace bands between 20,000 and 75,000 daltons. The major doublet at 20,000 and two minor bands at 70,000 and 28,000 appear to correspond to bands within the pre-selected horse serum population. Only particular lots of horse serum can be used to grow uncommitted stem cells in culture without their commitment to a fibrogenic phenotype. Of 55 lots of horse serum tested thus far only three lots have shown this activity: two from Sigma TM and one from Whittaker TM. These three horse sera were lyophilized and run on SDS-PAGE to compare their proteins with those contained within the myogenic isolate.

As shown by the following examples, this material stimulates myogenesis in vitro and in vivo, unlike any other known factor that stimulates proliferation of muscle cells.

EXAMPLE 3: EFFECTS OF MYOGENIC PROTEIN ISOLATE ON IN VITRO DIFFERENTIATION

Fertilized White Leghorn chick eggs were candled on day 3 and windowed to assess viability in accordance with the method of Young et al., *J. Histochem. Cytochem.* 37:223–228 (1989). On day 11 the embryos were removed from their eggs, decapitated, and their legs (encompassing knee to ankle joint) were removed and placed into sterile Tyrode's TM buffer in accordance with the method of Young et al., *Connec. Tiss. Res.* 17:99–118 (1989).

The skin was removed from each leg and the muscle and associated soft tissues dissected free from the cartilage and bone. The muscle tissues were finely minced, triturated to disperse cells, filtered through cheese cloth and through a 20 μm Nitex TM filter to obtain a single cell suspension. Viable cell numbers were estimated by the dye exclusion test: a 100 μl of cell suspension was mixed with 100 μl of 0.4% trypan blue in sterile Tyrode's TM solution at pH 7.4, and cells were counted on a hemocytometer. The cells were plated at $2.5 > 10^6$ cells per 100 mm dish and fed daily with Eagle's TM Minimal Essential Medium (MEM) containing Earle's TM salts (GIBCO, Gaithersburg, MD), 10% pre-selected horse serum, and 5% stage-specific embryo extract. This medium mixture was designated as plating differentiating medium. Cultures were incubated at 37° C. in a humidified 95% air/5% $CO_2$ incubator.

The cultures were maintained until all myogenic lineage committed cells had formed multinucleated spontaneously contracting myotubes embedded within multiple layers of mononucleated cells until confluency was reached and then replated at lower cell densities for testing various extract fractions. The cultures were gently trypsinized with 0.05% trypsin in Moscona's:-Moscona's TM -EDTA for 5–10 minutes at ambient temperature in accordance with the method of Young et al., *J. Tiss. Cult. Method.* 13: (1991).

The cell/trypsin suspension was added to one-half digestate volume of horse serum to inhibit further trypsin activity and was centrifuged. The supernatant was discarded, the cells resuspended in incomplete Eagle's TM Minimal Essential Media with Earle's TM salts, screened through cheese cloth and a 20 μm Nitex TM, and 100 μl of the single cell suspension removed for viability testing and cell counting as described above. Cells were seeded at $0.1 \times 10^6$ cells per 35 mm dish in complete medium. The remaining cells were cryopreserved in 7.5% dimethylsulfoxide (DMSO)-containing Eagle's TM Minimal Essential Medium with Earle's TM salts, 10% pre-selected horse serum and 5% stage-specific embryo extract.

Twenty-four hours after plating, the initial medium was removed and fresh medium containing 0, 1, 5, 10, 20, 30, and 40 μg/ml of lyophilized water soluble bone proteins (based on dry weight measure), or the equivalent dry weight of tissue culture grade bovine serum albumin (BSA) (Sigma, St. Louis, MO) as a control, was replaced daily. Cultures were incubated as described above.

In each experiment, cultures were assayed on days 3 and 6 of treatment. On day 3, each set of four cultures were first scored for ability to contract, two cultures were returned to the incubator, and the remaining two cultures had their medium removed, rinsed with Tyrode's TM buffer, and fixed in Perfix TM (Fisher Scientific Group, Pittsburgh, PA) for 45 seconds. Both cultures were rehydrated with water, one stained with toluidine blue, the other remained unstained, and both made permanent with glycerin jelly in accordance with the procedure of Humason, Animal Tissue Techniques. W. H. Freeman and Co., San Francisco (1972). Both cultures were then assayed for fusion index within each dish, calculated by determining the number of nuclei residing within multinucleated structures divided by the total number of nuclei. Each dish was divided into 36 equal groups ($6 \times 6$ matrix) and then six groups along each diagonal (12 groups total) were counted and averaged to obtain the fusion index for each plate. On day six the remaining two cultures were removed, assayed for contractility, processed as above for bright field and phase microscopy, and also assayed for fusion index.

RESULTS

Twenty-four hours after replating and before treatment with either water soluble proteins or BSA, the cultures contained predominantly stellate-shaped cells, approximating a mesenchymal, multipolar-like appearance. The cultures were then fed complete medium plus equivalent amounts of either lyophilized myogenic protein isolate or, as a control, bovine serum albumin.

By three days in culture, the control cultures, e.g., the dishes incubated with complete medium only (0 μg/ml) or complete medium containing 1, 5, 10, 20, 30, or 40 μg/ml BSA, demonstrated two morphologically distinct cell types, stellate-shaped cells and spindle-shaped cells. Experimental cultures, incubated with complete medium containing 5–40 μg/ml of lyophilized water-soluble bone protein isolate, displayed varying quantities of stellate-shaped cells and large branched multinucleated structures.

After six days of treatment, both control and protein isolate-containing cultures displayed confluent cell layers. The control cultures contained mononucleated spindle-shaped cells demonstrating swirl patterns and having a fusion index of less than 1% as shown in Table 1 below. The protein isolate-containing cultures displayed linear and branched multinucleated structures that spontaneously contracted and demonstrated a range of fusion indices dependent on the quantity of extract. The highest fusion index, 95%, occurred with 10 µg/ml of lyophilized water soluble protein extract as shown in Table 1 below.

TABLE 1

Percent Fusion Index of Avian Stem Cell Cultures Six Days After Treatment

| Protein Concentration | BSA ± SD | n | W-SP ± SD | n |
|---|---|---|---|---|
| 0.0 g/ml | 10 ± 2 | 72 | 10 ± 2 | 72 |
| 1.0 g/ml | <1 ± 1 | 48 | 10 ± 2+ | 48 |
| 5.0 g/ml | <1 ± 1 | 72 | 40 ± 3+,* | 72 |
| 10.0 g/ml | <1 ± 1 | 72 | 95 ± 5+,** | 72 |
| 20.0 g/ml | 1 ± 1 | 72 | 30 ± 5+,* | 72 |
| 30.0 g/ml | <1 ± 1 | 12 | 10 ± 5+ | 12 |
| 40.0 g/ml | 1 ± 1 | 36 | 5 ± 3 | 36 |

EXAMPLE 4: EFFECTS OF MYOGENIC PROTEIN ISOLATE ON IN VIVO DIFFERENTIATION

Implant material was prepared by mixing 20 mg dry weight of the lyophilized water soluble bone proteins with 20 mg of atelo type-I collagen supplied as 3 mg/ml solution in 0.01 n HCl (Vitrogen TM, Collagen Corp., Palo Alto, CA) and adding 1.5 ml of 8 M GuHCl to yield a final concentration of 2.7 M GuHCl. The solution was transferred to a dialysis bag and dialyzed five times against distilled water at 4° C. (1:100 ratio) then three times against 95% ethanol. The solution was then lyophilized in a sterile container prior to implantation.

Controls consisted of 20 mg of atelo type-I collagen plus 20 mg dry weight of BSA and processed as described above.

Breeding-age adult male mice were anesthetized by Metophane TM inhalation, the operational area was swabbed with 70% ethanol, and a small incision made in the skin. For the intramuscular pouch model, a small pouch in the back of the thigh (semimembranosus, semitendinosus) musculature was created by blunt dissection.

A bioerodible, surface-eroding polymer matrix delivery system or delivery vehicle having the myogenic protein isolate or a control interspersed throughout the matrix was prepared as described in U.S. patent application Ser. No. 07/742,264 to Laurencin et al., filed Aug. 7, 1991, which is incorporated herein by reference.

No delivery vehicle (control), delivery vehicle only (control), BSA/delivery vehicle (control), or the lyophilized water soluble bone protein isolate delivery vehicle (experimental) was implanted within the intramuscular pouch and the skin stapled closed. The mice were placed under a heat lamp, containing an incandescent light bulb, during postoperative recovery to maintain body heat and returned to their respective cages.

At tissue harvest, mice were euthanized with ether, staples removed, and the implant area plus 2-4 mm of surrounding tissue was removed for histological analysis. The tissues were fixed in 10% neutral buffered formalin, water washed, and processed for Paraplast TM embedment and serial sectioning at 5 µm in accordance with the method of Young et al., Anat. Rec. 212:183-194 (1985).

Alternate slides containing tissue sections were stained in either toluidine blue in accordance with the method of Young et al., J. Morph. 201:85-103 (1989) and assayed for early stage myogenic profiles within the implant, within the connective tissue scar immediately adjacent to and surrounding the implant, and along the scar:transected adult muscle tissue interface. Early stage myogenic profiles were characterized by the presence of multinucleated myotubes and/or small diameter myofibers with centrally located nuclei.

RESULTS

Histological analysis of the control implants, composed of no delivery vehicle, delivery vehicle only, or lyophilized bovine serum albumin/delivery vehicle, demonstrated the appearance of small regenerating myotubes at the scar:transected adult muscle tissue interface. The remaining portion of the operational field surrounding the area of the implant consisted of a dense interwoven connective tissue scar.

In contrast, histological analysis of experimental implants, consisting of lyophilized water-soluble proteins/delivery vehicle, revealed the presence of small regenerating myotubes at the scar:transected adult muscle tissue interface as well as linear multinucleated structures embedded within the connective tissue scar immediately adjacent to and surrounding the implant.

The small myotubes embedded within the connective tissue scar were present in approximately 90% of the mice implanted with the lyophilized myogenic bone protein isolate. The remaining approximate 10% of the mice implanted with lyophilized myogenic bone protein isolate displayed small regenerating myotubes near the adjacent transected adult musculature and massive inflammatory responses rather than connective tissue scars within the remaining tissues of the operational field.

EXAMPLE 5: MYOGENIC STIMULATION OF ISOLATED UNCOMMITTED STEM CELLS BY MUSCLE MORPHOGENETIC PROTEIN IN VITRO

A study was conducted to examine the ability of muscle morphogenetic protein (MMP) to induce a myogenic differentiative response in stem cells derived from cell isolates of leg skeletal muscle/epimysium/tendons, dermis, and periosteum/perichondrium. Plated mesenchymal-like cells were fed daily with 10 µg/ml of either bovine serum albumin (BSA) or MMP. Fusion index and spontaneous contractility on day six of culture were used to assess the myogenic differentiation response. After six days, all cultures incubated with BSA demonstrated confluent spindle-shaped cells, no spontaneous contractility, and a fusion index of less than 1%. Treatment of sister cultures with MMP elicited confluent linear and branched multinucleated cells displaying spontaneous contraction. The results demonstrate that populations of uncommitted stem cells are present within various connective tissue matrices in the leg and that MMP can stimulate a muscle phenotype within these populations.

It is known that demineralized bone matrix will stimulate the differentiation of chondrocytes from uncommitted stem cells located in the connective tissue of several organs. To determine whether stem cells capable of differentiating into muscle are similarly widespread, mononucleated mesenchymal-like cells were isolated from muscle, epimysium/tendon, dermis, and periosteum/perichondrium by differential plating/replating. These cells were then tested for their ability to differentiate into a muscle-like phenotype under the influence of an optimal concentration of MMP.

Small windows were cut into candled, fertilized white Leghorn chick embryos to assess viability using the method of Young, et al., *J. Histochem. Cytochem.* 37:223-228 (1989). On days 9, 11, 14, and 17 of development embryos were sacrificed according to NIH Guidelines for Animal Welfare. The embryos were removed from their eggs, decapitated, their legs (encompassing ankle to knee joints) were removed according to the method of Young, et al., *J. Morph.* 201:85-103 (1989) and placed into sterile Tyrode's TM buffer (Young et al., *Conn Tiss. Res* 17:99-118 (1989). The skin was removed from each leg and pooled. The muscle and associated connective tissues (i.e., tendons, epimysium, perimysium, and endomysium) were dissected free from the bone and cartilage. The periosteum and perichondrium were gently stripped from the bone and cartilage and pooled. Muscle myofibers were gently teased to remove as much of the adherent connective tissue as possible. The tendons were severed from the distal ends of the muscle and the epimysium and tendons pooled. The tissues in each pool (i.e., myofibers with associated endomysium and perimysium, epimysium/tendons, dermis, and periosteum/perichondrium) were finely minced to dissociate the mononucleated cells from the structural elements. Each tissue group was filtered through sterile cheese cloth to removed large clumps, filtered through sterile 20 $\mu$m Nitex to remove cell aggregates, and 100 $\mu$l of the single cell suspension was added 1:1 with 0.4% trypan blue in sterile Tyrode's TM buffer for the dye exclusion test to determine cell viability and estimate cell numbers. The cells were initially plated at $2.5 \times 10^5$ cells in 100 mm dishes coated with 1% gelatin in Eagle's TM Minimal Essential Medium with Earle's TM salts (GIBCO) containing the antibiotics: penicillin G at 100,000 U/L, streptomycin at 100,000 $\mu$g/L (GIBCO), 10% preselected horse serum (Sigma), 5% stage-specific embryo extract, and designated as complete medium. Fresh complete medium was replaced daily. Cultures were incubated at 37° C. in a humidified 95% air/5% $CO_2$ environment.

Cultures were maintained under these optimum conditions for cellular differentiation for six days. On day six, cultures were gently trypsinized with 1% trypsin: Moscona's TM :Moscona's TM -EDTA at a v/v/v ratio of 2:19:19 for 5-10 min at ambient temperature. When individual cells or cell layers lifted off the dish with gentle swirling, the cell/enzyme mixture was gently triturated 20 times, in a 10 ml pipet, to dissociate single mononucleated cells from differentiated structures, added to $\frac{1}{2}$ volume of pre-selected horse serum to neutralize the trypsin, and then centrifuged at 3254 g for 17 min. The supernatant was discarded and the cells were resuspended in incomplete Eagle's TM medium (without horse serum or embryo extract). This cell/medium mixture was sieved through sterile cheese cloth, sterile 20 $\mu$m Nitex and 100 $\mu$l of the single cell suspension removed for cell viability analysis and estimation of cell numbers. The resultant mononucleated cell populations from each tissue source were seeded at either $10^5$ cells per 35 mm-1% collagen coated dish or $5 \times 10^3$ cells/-well in a 1% gelatin coated 24-well plate in complete medium containing 10 $\mu$g (dry weight) /ml of either lyophilized muscle morphogenetic proteins (MMP), derived from a 4 M guanidine hydrochloride extract of 0.6 N HCl demineralized bovine bone matrix, as the experimental treatment, or tissue culture grade bovine serum albumin (BSA, Sigma) as control treatment. Four sets of cultures were used per time point per day stage, with each experiment repeated a minimum of three separate times.

The cultures were assayed on days three and six of treatment for spontaneous contraction and fusion index. The fusion index is defined here as the number of nuclei residing within multinucleated structures divided by the total number of nuclei and then multiplied by 100. Each set of four cultures were first scored for spontaneous contractility, medium removed, rinsed with sterile Tyrode's solution, fixed in Perfix (Fisher) for 45 sec, rehydrated with water, one set remained unstained while the other set was lightly stained in 0.1% Toluidine blue (Fisher), and both made permanent with glycerin jelly, Humason, *Animal Tissue Techniques* (San Francisco, W. H. Freeman and Co. 1972). Both culture sets were then assayed for percent fusion index with both phase (unstained cultures) and bright field (toluidine blue-stained cultures) microscopy. Each dish was divided into 36 groups and then six groups along each diagonal (12 groups total) were counted and averaged to obtain the fusion index for each plate. The variation in the averaged fusion indices between control and experimental treatments were analyzed using the Paired Student's T-test (Sokal and Rohlf, *Biometry. The Principles and Practice of Statistics in Biological Research* (San Francisco, W.H. Freeman and Co. 1969) for equal sample sizes. Significance was noted if the P-value was less than 0.05.

RESULTS

Twenty-four hours after plating of the primary tissue isolates from muscle, epimysium/tendon, dermis, and periosteum/perichondrium, all cultures consisted of three morphologically distinct cell types: stellate-shaped cells, spindle-shaped cells, and bipolar-shaped cells. Six days incubation in complete medium elicited multiple confluent layers of stellate-shaped cells with embedded linear and branched myotubes exhibiting spontaneous contraction. Twenty-four hours after replating confluent monolayers, cultures from all primary tissue isolates (muscle, epimysium/tendon, dermis, and periosteum/perichondrium) consisted of mononucleated stellate-shaped cells.

Incubating replated stem cell cultures for three days in complete medium containing BSA elicited two morphologically distinct mononucleated cell types: stellate-shaped cells and spindle-shaped cells. Sister cultures, incubated for three days with MMP, displayed predominantly two morphologically distinct cell types, mononucleated stellate-shaped cells and variously-sized linear and branched multinucleated cells. The largest multi-branched multinucleated cells were present in cultures generated from isolated muscle tissues, branched multinucleated cells of slightly smaller size arose from cultures generated from epimysium/tendon, intermediate branched multinucleated cells were present in cultures generated from dermis, while smaller linear to intermediate branched multinucleated cells arose in cultures generated from periosteum/perichondrium isolates.

Six days incubation of control cultures with bovine serum albumin elicited a confluent cell layer of mononucleated spindle shaped cells exhibiting swirl patterns and having a fusion index of less than 1%. Six days incubation of cultures from all primary tissue isolates with muscle differentiative factors elicited confluent layers consisting of stellate-shaped cells and linear and branched myotube-like structures that spontaneously contracted and displayed a range of fusion indices. Progenitor cells isolated from muscle demonstrated a 95% fusion index, from epimysium/tendon demonstrated a 90% fusion index, from dermis demonstrated a 75% fusion index, and from periosteum/perichondrium demonstrated a 50% fusion index. There was no detectable or statistically significant difference in either spontaneous contractility or fusion index, comparing stem cells derived from primary tissue isolates from day 9, 11, 14, or 17 of development and treated with muscle morphogenetic proteins.

Previously only Levander, *Induction Phenomenum and Tissue Regeneration* (Williams and Wilkins, Baltimore 1964), Polezhaev (1977), and a small number of other investigators, reviewed by Bruce M Carlson, *Am. J. Anat.* 137:119-150 (1979) have reported the formation of skeletal muscle fibers in the connective tissue scarring surrounding their implants. The results from their experiments suggest at least two possibilities for the origin of myogenic stem cells that would give rise to the connective tissue embedded myogenic-like structures. One suggestion is the recruitment of satellite cells from the distant damaged skeletal muscle fibers. An alternate possibility suggests the presence of quiescent resident stem cells located among the connective tissue matrices.

Previous experimentation (Snow, *Anatomical Record* 188:181-199 (1977), 188:200-218 (1977); Schultz, *Anat. Rec.* 208:501-506 (1984); Schultz et al., *Muscle and Nerve* 8:217-222 (1985); Bischoff, *Muscle Regeneration* 13-29 (Raven Press 1979), Bischoff, *Dev. Biol.* 115:129-139 (1986), Bischoff, *Dev. Biol.* 115:140-147 (1986) has demonstrated both a proliferative and migratory response of satellite cells to focal injury of muscle fibers. However, the reported migratory activities of the satellite cells were localized to areas directly adjacent to the damaged muscle fibers. Therefore, it is presently unknown whether satellite cells will migrate over relatively large distances into the surrounding connective tissue and participate in muscle regeneration.

Alternatively, studies by Polezhaev (1977) with skeletal muscle pieces soaked in a 1.0% aqueous solution of trypan blue (Gurr Co., #2691) for 48 hrs and then implanted within the omentum of rats and rabbits describes formation of muscle fibers in the surrounding connective tissue scar. While Polezhaev's study (1977) is a follow-up of earlier work by Levander (1964), it does not address the issue of the actual source of the myogenic stem cells responsible for the myotubes within omentum. An alternate interpretation of their findings might be that satellite cells within the trypan blue-treated skeletal muscle mince survived the initial treatment, where the differentiated myofibers did not. Upon implantation in the omentum, the differentiated myofibers degenerated while surviving satellite cells proliferated, fused, and formed the regenerated myotubes.

As an initial attempt to address the origin of the stem cells forming the myotube-like structures within the connective tissue scar, mononucleated stellate-shaped mesenchymal-like cells were isolated from various connective tissue matrices from day 9-17 embryonic chick legs. However, due to the intimate nature of the tissues involved, i.e., myofibers/endomysium/perimysium, epimysium/tendon, dermis, and periosteum/perichondrium, 1989b), contamination of the non-skeletal muscle cultures by stray satellite cells could have been possible. To control for that possibility, differential plating/replating procedure was used. This procedure promotes the differentiation of lineage-committed stem cells (satellite cells, chondroblasts, etc.) into their adult differentiated phenotype (myotubes, chondrocytes, etc.) while maintaining non-committed cells in a mesenchymal-like undifferentiated state almost indefinitely by incubating with the primary culture medium. These undifferentiated mesenchymal-like cells were then treated with BSA or MMP under conditions conducive for differentiation. The results demonstrated a mononucleated fibroblastic-like cell type for those cultures treated with BSA, while multinucleated spontaneously contracting cells were present, in varying quantities, in all cultures treated with MMP.

EXAMPLE 6: COMPARISON OF MYOGENIC ISOLATE WITH KNOWN INDUCER OF MUSCLE CELL PROLIFERATION

Cryopreserved uncommitted stem cells were thawed, reconstituted in plating medium using a 1:19 volume ratio of cell suspension to plating medium. The mixture was centrifuged, supernatant removed to remove DMSO, and cells resuspended in plating medium and 100 μl of single cell suspension removed for viability testing and cell counting as described above.

Cells were plated at 5,000 cells per well of a 24-well tissue culture plate in 1.0 ml of plating medium. Twenty-four hours later the plating medium was replaced with testing medium, i.e., Eagle's Minimal Essential Medium containing Earle's salts with 15% Ultraculture (Whittaker). Twenty hour later, the testing medium was replaced with testing medium plus materials to be tested. Materials tested were: 0.1 to 2.0 μg insulin/ml (Sigma), 1 to $-10-10^{-6}$ M dexamethasone (Sigma), 0.001 to 500 ng Insulin Growth Factor I/ml (Chemicon), 0.001 to 500 ng Insulin Growth Factor II/ml (Chemicon), and 0.1 to 1000 ng MMP/ml. Cells were treated for three days and then assayed for myosin content (used as a measure of myogenic induction) and DNA content (used as a measure of cellular proliferation) using a myosin-enzyme linked immunoculture assay (Myosin-ELICA). The medium was removed from the cultures, they were rinsed with Tyrode's TM buffer and fixed in $-20°$ C. methanol for 5 min. The methanol was removed, the cultures rinsed with Tyrode's TM buffer, and treated with 0.1% Triton-X10 TM (Sigma) to solubilize cell membranes, rinsed with Tyrode's TM treated with 0.03% sodium azide (Sigma) to irreversibly inhibit endogenous peroxidases, rinsed with 2% milk protein in Tyrode's TM buffer and incubated with MF-20 TM monoclonal antibody (Developmental Biology Hybridoma Facility, Iowa City, IA), an antibody against adult sarcomeric myosin, Bader, et al., *J. Cell Biol.* 95:763-770 (1982). The antibody was removed, the cultures rinsed with 2% milk protein in Tyrode's TM buffer, and then incubated with biotinylated goat anti-mouse IgG (Fisher Biotek). This second antibody was removed, the cultures rinsed with Tyrode's TM, and then incubated with Avidin-HRP TM (Vector Laboratories). This segment was removed, the cultures rinsed with Tyrode's TM, and incubated with ABTS TM (Kirkegard and Perry Laboratories) (ABTS is a soluble chromagen and horse radish peroxidase (HRP) substrate that when reacted with HRP will turn from a soluble clear material to a colored product). Two hundred microliters of ABTS solutions from each well were transferred to respective wells within a 96-well plate containing 10 μl of 0.03% sodium azide to stop the reaction, and then read in a 96-well multichannel plate reader/spectrophotometer at 405 nm. The remaining solutions in the 24-well plate were removed, rinsed with Tyrode's ™ buffer and incubated with an insoluble precipitated HRP substrate, i.e., 4-chloro-1-napthol (Sigma), 0.03% sodium azide added to stop the reaction, and photographed. The solution were removed, the cultures rinsed with Tyrode's ™ buffer and processed for DNA analysis in accordance with the method of Young, et al., *J. Tiss. Cult. Metho.* 13:275–288 (1991).

RESULTS

Control (non-treated) cultures demonstrated a myosin content of 1.5 ng myosin per microgram DNA; 2000 ng insulin/ml demonstrated maximal myogenic inducing activity of 4.6 ng myosin/$\mu$g DNA; $10^{-8}$ M dexamethasone/ml demonstrated maximal activity at 9.5 mg/ml; 200 ng/ml IGF-I stimulated myosin content to 9.6 ng myosin/$\mu$g DNA; 200 ng/ml IGF-II stimulated myosin content to 12.8 ng myosin/$\mu$g DNA; and 200 ng/ml of myogenic isolate (MMP) induced myogenesis as noted by 60.2 ng myosin/$\mu$g DNA.

Modifications and variations of the myogenic protein isolate and methods of use thereof, will be obvious to those skilled in the art from the foregoing description. Such modifications and variations are intended to come within the scope of the appended claims.

We claim:

1. A protein isolate comprising one or more water soluble proteins isolated from mammalian bone, wherein the protein isolate selectively stimulates stem cell myogenic lineage commitment and differentiation into myotubes and multinucleated structures in vitro and in vivo, contains proteins having molecular weights between 50,000 and 200,000 daltons, does not bind to DEAE in urea at pH 6.0, and binds to a cation exchange column at pH 6.0.

2. The protein isolate of claim 1 wherein the protein isolate selectively stimulates myogenic stem cell differentiation into functional muscle tissue in vivo.

3. A method of inducing myogenesis n undifferentiated stem cells in culture or in a patient in need of treatment thereof comprising administering a therapeutically effective amount of between approximately 1 ng and 10 mg per kilogram of stem cells or body weight of a water soluble protein isolate extracted from mammalian bone to the stem cells to induce myogenic lineage commitment and differentiation into myotubes and multinucleated structures, wherein the protein isolate contains proteins having molecular weights between 50,000 and 200,000 daltons, does not blind to DEAE in urea at pH 6.0, and binds to a cation exchange column at pH 6.0.

4. The method of claim 3 wherein the protein isolate is administered to a wound in an amount effective to induce muscle repair.

5. The method of claim 3 wherein the administering step is performed by implanting in the patient in need thereof the protein isolate incorporated into a delivery vehicle that provides controlled release of the protein isolate at a site where myogenic stem cell differentiation is desired.

6. The method of claim 3 wherein the protein isolate is administered to the stem cells in culture or in the patient in need thereof in combination with a therapeutically effective amount of a compound selected from the group consisting of inducers of cell proliferation, antibiotics, and antiinflammatories.

7. The method of claim 2 wherein the patient to be treated has a disorder selected from the group consisting of muscular dystrophy, myasthenia gravis, multiple sclerosis, nerve block injuries, muscle atrophy, embryonic failure of myotomes to migrate, rhabdomyosarcoma, aneurysms, hemorrhage, ptosis, muscle tears, and muscle damaged by infarction.

8. The method of claim 5 wherein the delivery vehicle is a polymeric matrix.

9. The method of claim 8 wherein the polymeric matrix is selected from the group consisting of biocompatible bioerodible and non-erodible polymers.

10. The method of claim 9 wherein the bioerodible polymer is selected from the group consisting of surface eroding polymers and bulk eroding polymers.

* * * * *